United States Patent [19]

Varasi et al.

[11] Patent Number: 5,424,328

[45] Date of Patent: Jun. 13, 1995

[54] PHENYL-IMIDAZOLIDINONE DERIVATIVES

[75] Inventors: Mario Varasi, Milan; Franco Heidempergher, Parabiago; Carla Caccia, Gallarate; Claudio Arrigoni, Gambolò, all of Italy

[73] Assignee: Farmitalia Carlo Erba S.r.l., Milan, Italy

[21] Appl. No.: 144,514

[22] Filed: Nov. 2, 1993

[30] Foreign Application Priority Data

Nov. 18, 1992 [GB] United Kingdom ............... 9224144

[51] Int. Cl.⁶ .................. A61K 31/415; C07D 401/06
[52] U.S. Cl. ................................. 514/397; 548/314.4
[58] Field of Search .................. 548/314.4; 514/397

[56] References Cited

U.S. PATENT DOCUMENTS

| | | | |
|---|---|---|---|
| 3,459,757 | 8/1969 | Wright et al. | 260/294 |
| 3,491,098 | 1/1970 | Archer | 260/268 |
| 3,702,327 | 11/1972 | Li et al. | 260/293.66 |
| 4,600,430 | 5/1988 | Seiyaku | 71/92 |
| 4,886,817 | 12/1989 | Takeda et al. | 514/341 |
| 5,242,929 | 9/1993 | Varasi et al. | 514/305 |

FOREIGN PATENT DOCUMENTS

| | | |
|---|---|---|
| 0268229 | 5/1988 | European Pat. Off. . |
| 0323077 | 7/1989 | European Pat. Off. . |
| 0379990 | 8/1990 | European Pat. Off. . |
| 2288 | 2/1964 | France . |
| 61033172 | 2/1986 | Japan . |
| 62/4312 | 3/1963 | South Africa . |
| 67/412 | 11/1967 | South Africa . |

OTHER PUBLICATIONS

J. Med. Chem. 1970, 13(4), 623–6 by Lien, Eric J. et al.
Yao Hsueh Hsueh Pao 1981, 16 (1) 19–23 by Xiang Bing-Ren et al. C.A. 95:125880e.
J. Chem. Eng. Data, 1968, 13 (4) 582–5 by Knopf Robert J.
Journal of Medicinal Chemistry, vol. 9, 1966, Wasington US, pp. 852–857, W. B. Wright et al., "Central nervous system depressants. I. 1-Aminoalkyl-3-aryl derivatives of 2-imidazolidinone, 2-imidazolidinethione and therahydro-2(1H)-pyrimidinone".

Primary Examiner—Patricia L. Morris
Attorney, Agent, or Firm—Nikaido, Marmelstein, Murray & Oram

[57] ABSTRACT

The invention relates to new derivatives of 1-imidazolylalkyl-3-phenyl-imidazolidin-2-ones of general formula (I)

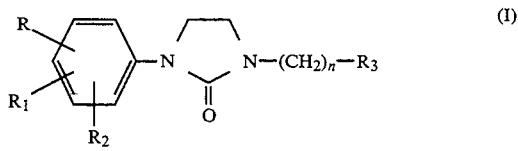

wherein
n is 1, 2 or 3; each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy-carbonyl, nitro, —N($R_4$ $R_5$) in which each of $R_4$ and $R_5$ independently is hydrogen $C_1$–$C_6$ alkyl formyl or $C_2$–$C_6$ alkanoyl; or a ($R_6$ $R_7$)N—$SO_2$ group, in which each of $R_6$ and $R_7$ independently is hydrogen or $C_1$–$C_6$ alkyl; $R_3$ is an imidazolyl group of formula

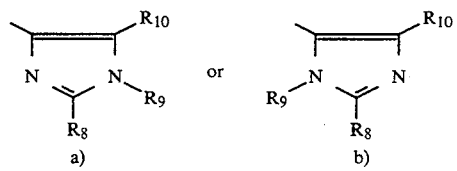

wherein each of $R_8$ and $R_{10}$ which may be the same or different is hydrogen or $C_1$–$C_6$ alkyl, $R_9$ is hydrogen, $C_1$–$C_6$ alkyl or a nitrogen protecting group, or pharmaceutically acceptable salts thereof, which are useful in the treatment of CNS disorders, such as, e.g., anxiety and psychosis, and in the treatment of gut motility disorders, and/or emesis.

6 Claims, No Drawings

PHENYL-IMIDAZOLIDINONE DERIVATIVES

The present invention relates to new derivatives of 1-imidazolylalkyl-3-phenyl-imidazolidin-2-ones, to a process for their preparation, to pharmaceutical compositions containing them and to their use as therapeutic agents. The present invention provides novel compounds having the general formula (I)

$$\text{(I)}$$

R—(phenyl ring with $R_1$, $R_2$)—N—(imidazolidinone ring, C=O)—N—$(CH_2)_n$—$R_3$ wherein n is 1, 2 or 3; each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy-carbonyl, nitro, —$N(R_4 R_5)$ in which each of $R_4$ and $R_5$ independently is hydrogen, $C_1$–$C_6$ alkyl, formyl or $C_2$–$C_6$ alkanoyl; or a $(R_6 R_7)N$—$SO_2$ group, in which each of $R_6$ and $R_7$ independently is hydrogen or $C_1$–$C_6$ alkyl;

$R_3$ is an imidazolyl group of formula a) imidazole with $R_{10}$, $R_9$, $R_8$ substituents   or   b) imidazole with $R_{10}$, $R_9$, $R_8$ substituents wherein each of $R_8$ and $R_{10}$ which may be the same or different is hydrogen or $C_1$–$C_6$ alkyl, $R_9$ is hydrogen, $C_1$–$C_6$ alkyl or a nitrogen protecting group; and the pharmaceutically acceptable salts thereof.

The formula reported above for the compounds according to the present invention includes all the possible isomers, as well as their mixtures.

The invention includes within its scope the metabolites and the metabolic precursors or bio-precursors (otherwise known as pro-drugs) of the compounds of formula (I). Namely, the invention includes compounds which have a different formula to formula (I) above, but which nevertheless upon administration to a human being are converted directly or indirectly in vivo into a compound of formula (I).

A halogen atom may be a fluorine, chlorine, bromine or iodine atom, preferably it is chlorine or bromine. The alkyl, alkenyl, alkynyl, alkoxy and alkylthio group may be a branched or straight chain group.

A $C_1$–$C_6$ alkyl group is preferably a $C_1$–$C_4$ alkyl group, e.g. methyl, ethyl, propyl, isopropyl, butyl, sec. butyl or tert. butyl, in particular methyl or ethyl.

A $C_1$–$C_6$ alkoxy group is preferably a $C_1$–$C_4$ alkoxy group, e.g. methoxy, ethoxy, propoxy, isopropoxy and butoxy, preferably methoxy and ethoxy.

A $C_1$–$C_6$ alkylthio group is preferably a $C_1$–$C_4$ alkylthio group, e.g. methylthio, ethylthio, propylthio and butylthio, in particular methylthio.

A $C_2$–$C_6$ alkanoyl group is e.g. a $C_2$–$C_4$ alkanoyl group, in particular acetyl and propionyl.

A nitrogen protecting group may be one of those employed usually in the chemistry of peptides, typically a triphenylmethyl, t-butyloxycarbonyl, benzyloxycarbonyl, acetyl, formyl, di(p-methoxyphenyl)methyl and (p-methoxyphenyl) diphenylmethyl.

Pharmaceutically acceptable salts of the compounds of formula (I) include acid addition salts, with inorganic, e.g. nitric, hydrochloric, hydrobromic, sulphuric, perchloric and phosphoric acids, or organic, e.g. acetic, propionic, glycolic, lactic, oxalic, malonic, fumaric, malic, maleic, tartaric, citric, benzoic, cinnamic, mandelic and salicylic acids.

Preferred compounds of the invention are the compounds of formula (I) wherein each of R, $R_1$ and $R_2$, which may be the same or different, is hydrogen, halogen, cyano, $C_1$–$C_4$alkyl, $CF_3$, $C_1$–$C_4$ alkylthio, $C_1$–$C_4$ alkoxy or —$N(R_4 R_5)$ in which each of $R_4$ and $R_5$ independently is hydrogen, $C_1$–$C_4$ alkyl, formyl or $C_2$–$C_4$ alkanoyl;

n is 1 or 2;

$R_3$ is as defined above;

each of $R_8$, $R_9$ and $R_{10}$ is independently hydrogen or $C_1$–$C_4$ alkyl; and the pharmaceutically acceptable salts thereof.

Examples of preferred compounds according to the invention are the following:

1-(5-methyl-1H-imidazol-4-yl)methyl-3-(3-chlorophenyl)-imidazolidin-2-one;
1-(5-methyl-1H-imidazol-4-yl)methyl-3-phenyl-imidazolidin-2-one;
1-(5-methyl-1H-imidazol-4-yl)methyl-3-(3-bromophenyl)-imidazolidin-2-one;
1-(5-methyl-1H-imidazol-4-yl)methyl-3-(3-cyanophenyl)-imidazolidin-2-one;
1-(5-methyl-1H-imidazol-4-yl)methyl-3-(3-methylthiophenyl)-imidazolidin-2-one;
1-(5-methyl-1H-imidazol-4-yl)methyl-3-(3-methylphenyl)-imidazolidin-2-one;
1-(5-methyl-1H-imidazol-4-yl)methyl-3-(3,5-dimethylphenyl)-imidazolidin-2-one;
1-(5-methyl-1H-imidazol-4-yl)methyl-3-(3,5-dichlorophenyl)-imidazolidin-2-one;
1-(1H-imidazol-4-yl)methyl-3-(3-chlorophenyl)-imidazolidin-2-one;
1-(1H-imidazol-4-yl)methyl-3-phenyl-imidazolidin-2-one;
1-(1H-imidazol-4-yl)methyl-3-(3-bromophenyl)-imidazolidin-2-one;
1-(1H-imidazol-4-yl)methyl-3-(3-cyanophenyl)-imidazolidin-2-one;
1-(1H-imidazol-4-yl)methyl-3-(3-methylthiophenyl)-imidazolidin-2-one;

and the pharmaceutically acceptable salts thereof, in particular the hydrochloride.

The compounds of the invention and the salts thereof can be obtained by a process comprising:

a) reacting a compound of formula (II), or a salt thereof $$\text{(II)}$$

R—(phenyl ring with $R_1$, $R_2$)—N—(imidazolidinone ring, C=O)—N—H wherein R, $R_1$ and $R_2$ are as defined above, with a compound of formula (III)

$$R_3\text{–}(CH_2)_n\text{–}Y \quad \text{(III)}$$

wherein n is as defined above, Y is a leaving group and in R₃, which is as defined above, R₉ is C₁-C₆ alkyl or a nitrogen protecting group, thus obtaining a compound of formula (I) wherein R₉ is as defined above bar hydrogen; or b) deprotecting a compound of formula (IV)

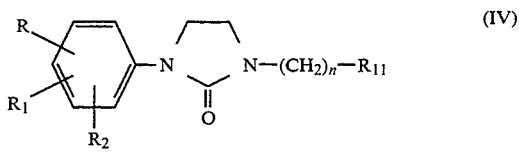

wherein R, R₁, R₂ and n are as defined above and R₁₁ is a group of formula

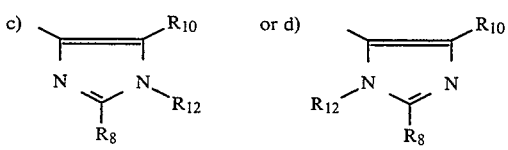

wherein R₈ and R₁₀ are as defined above and R₁₂ is a nitrogen protecting group, thus obtaining a compound of formula (I), wherein R₉ is hydrogen; and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of compounds of formula (I) into the single isomers.

A salt of a compound of formula (II) may be for example an alkali metal salt, preferably a sodium or potassium salt.

The salification of a compound of formula (II) may be performed according to known methods, e.g. by treatment with an alkaline hydride, preferably sodium hydride, or with lithium diisopropylamide or an alkaline alkoxide, preferably potassium tert-butylate.

In a compound of formula (III) Y as a leaving group may be for example a halogen atom, typically chlorine, iodine or bromine, in particular chlorine; or the residue of a reactive ester, typically the residue of a reactive ester of an alcohol, in particular a sulfonyloxy derivative e.g. a mesyloxy or tosyloxy, more preferably a mesyloxy group.

The reaction of a compound of formula (II), or a salt thereof, with a compound of formula (III) can be performed for instance in an anhydrous aprotic organic solvent e.g. dimethylformamide, dimethylacetamide or in other organic solvents e.g. toluene, tetrahydrofuran or dioxane, at temperatures ranging from about −10° C. to reflux temperature, in the presence of a basic agent e.g. NaH or potassium tertbutylate.

The deprotection of a compound of formula (IV) can be carried out according to known methods such as hydrolysis, for example acidic hydrolysis, for instance using an aqueous solution of halo-hydric acids, typically HCl or HBr, or diluted sulphuric acid, or aqueous acetic acid, at a temperature ranging from room temperature to reflux temperature.

Alternatively the deprotection may be carried out by treatment with trifluoroacetic acid in an organic aprotic solvent, e.g. in methylene chloride, chloroform or carbonium tetrachloride, at a temperature ranging from room temperature to reflux temperature.

A compound of formula (I) can be converted, if desired, into another compound of formula (I) according to known methods. Thus for instance a compound of formula (I), wherein one or more of R, R₁ and R₂ is amino can be converted into another compound of formula (I) wherein one or more of R, R₁ and R₂ is C₂-C₆ alkanoylamino or formylamino.

A compound of formula (I) in which one or more of R, R₁ and R₂ is carboxy can be converted into another compound of formula (I) wherein one or more or R, R₁ and R₂ is C₁-C₆ alkoxycarbonyl, and vice versa. These optional conversions can be carried out by methods known in themselves.

A compound of formula (I) wherein R₉ is hydrogen may be converted into another compound of formula (I) wherein R₉ is C₁-C₆ alkyl, by following well known procedures, for example as described above as to the reaction of a compound of formula (II) with an alkylating agent of formula (III). For example a compound of formula (I) wherein one or more of R, R₁ and R₂ is hydroxy may be converted into the respective compound of formula (I) wherein one or more of R, R₁ and R₂ is C₁-C₆ alkoxy by reaction with a suitable alkyl halide in the presence of a base such as NaOH, KOH, Na₂CO₃, K₂CO₃, NaH, NaNH₂, sodium methoxide or sodium ethoxide, in a solvent selected from the group consisting, for example, of methanol, ethanol, dioxane, acetone, dimethylformamide, hexamethylphosphoramide, tetrahydrofuran, water and their mixtures at a temperature ranging preferably between about 0° C. and 70° C.

Furthermore, a compound of formula (I) wherein one or more of R, R₁ and R₂ is C₁-C₆ alkoxy may be converted into the respective compound of formula (I) wherein one or more of R, R₁ and R₂ is hydroxy, for example, by treatment with pyridine hydrochloride or with a strong acid such as HBr or H I, or with a Lewis acid such as AlCl₃ or BBr₃ or with an alkaline salt of a thiol.

Also the reduction of a compound of formula (I) wherein one or more of R, R₁ and R₂ is nitro into the corresponding compound of formula (I) wherein one or more of R, R₁ and R₂ is amino may be carried out by known procedures, e.g. by catalytic hydrogenation and using preferably Pd/C as catalyst.

Alkylation of a compound of formula (I) wherein one or more of R, R₁ and R₂ is amino may be carried out for example by reaction of a suitable C₁-C₆ alkyl halide in the presence of a base such as Na₂CO₃, K₂CO₃, NaH or NaNH₂, in a solvent such as dimethylformamide, dimethylacetamide, dioxane, tetrahydrofuran or their mixtures, at a temperature varying between room temperature and about 100° C. Said alkylation process provides a mixture of N,N′ dialkylated compounds of formula (I). The single alkylated compounds may be separated from the mixture according to well known methods, e.g. by silica gel column chromatography.

The optional salification of a compound of formula (I) as well as the conversion of a salt into the free compound and the separation of a mixture of isomers into the single isomers may be carried out by conventional methods.

When in the compounds described above groups are present which need to be protected during the reactions described above, such groups can be protected in a conventional way before the reaction takes place and then deprotected. Examples of protecting groups are those employed usually in the chemistry of peptides.

The compounds of formula (II) are either known or may be obtained according to known methods e.g. as described in J. Med. Chem., 9, 852 (1966).

The compounds of formula (III) are known or may be obtained by known methods.

The compounds of the invention are active on the serotoninergic system, in particular as $5HT_3$ receptor antagonists, as proven for example by the fact that they have been found to be active in antagonizing the von Bezold-Jarisch chemoreflex evoked by 5-HT in the anesthetized rat according to the method described by Fozard J. R., Naunyn-Schmiedeberg's Arch. Pharmacol. 326, 36–44 (1984).

The following Table I reports the in vivo $5HT_3$ antagonist activity data obtained in this test for a representative group of compounds of the invention.

TABLE I

Inhibition of the Bezold-Jarisch reflex elicited by 5-HT (20 ug/kg i.v.) by i.v. FCE-compounds in the anesthetized Values are mean ± S.E.M. from 6 animals.

| Compound | Dose (μg/kg i.v.) | % inhibition | $ED_{50}$ (μg/kg) (limits) |
|---|---|---|---|
| FCE 27733 | 1 | 7.0 ± 6.0 | 5.26 |
| | 3 | 37.8 ± 5.8* | (4.51–6.06) |
| | 10 | 89.7 ± 1.8* | |
| FCE 28277 | 1 | 14.7 ± 3.8* | 3.9 |
| | 3 | 37.4 ± 6.5* | (3.1–4.9) |
| | 10 | 79.4 ± 4.1* | |
| FCE 28159 | 3 | 30.0 ± 5.9* | 6.5 |
| | 10 | 64.2 ± 5.0* | (4.6–8.4) |
| | 30 | 84.4 ± 4.2* | |
| FCE 28276 | 10 | 14.3 ± 9.2* | 32.2 |
| | 30 | 44.5 ± 7.3* | (23.7–44.2) |
| | 100 | 87.7 ± 7.0* | |
| FCE 28278 | 10 | 16.8 ± 8.1* | 28.6 |
| | 30 | 54.7 ± 2.3* | (23.2–35.0) |
| | 100 | 85.8 ± 1.2* | |
| FCE 28232 | 0.5 | 1.5 ± 4.8 | 2.2 |
| | 1 | 18.2 ± 2.4* | (1.9–2.6) |
| | 2 | 55.5 ± 7.1* | |
| | 8 | 88.7 ± 1.8* | |
| FCE 28355 | 1 | 14.6 ± 7.3* | 3.1 |
| | 3 | 51.1 ± 4.3* | (2.5–3.9) |
| | 10 | 83.3 ± 3.5* | |
| FCE 28356 | 100 | 88.6 ± 2.4* | n.c. |
| FCE 28307 | 100 | 56.1 ± 10.3* | n.c. |
| Vehicle | — | −1.8 ± 2.2 | — |

*p < 0.01 vs controls (Dunnett's test).

The affinity for serotonin $5-HT_3$ receptors was assessed for instance in rat entorhinal cortex using a selective radioligand $3H$-BRL 43694 as described by Nelson and Thomas (1989).

NELSON D. R. and THOMAS D. R., [3H]-BRL 43694 (Granisetron), a specific ligand for $5-HT_3$ binding sites in rat brain cortical membranes, Biochem. Pharmac., 38, 1693–1695, 1989. The affinity data for a representative group of compounds of the invention are set out in following Table II.

| Compound | 3H - BRL 43694 $IC_{50}$, nM |
|---|---|
| FCE 27733 | 2.1 |
| FCE 28277 | 14 |
| FCE 28159 | 2.7 |
| FCE 28276 | 11 |
| FCE 28278 | 6.7 |
| FCE 28232 | 0.42 |
| FCE 28355 | 4 |
| FCE 28356 | 1.8 |

-continued

| Compound | 3H - BRL 43694 $IC_{50}$, nM |
|---|---|
| FCE 28307 | 44 |

In the tables
FCE 27733 means: 1-(5-methyl-1H-imidazol-4-yl)methyl-3-(3-chlorophenyl)-imidazolidin-2-one;
FCE 28277 means: 1-(5-methyl-1H-imidazol-4-yl)methyl-3-phenyl-imidazolidin-2-one;
FCE 28159 means: 1-(5-methyl-1H-imidazol-4-yl)methyl-3-(3-bromophenyl)-imidazolidin-2-one;
FCE 28276 means: 1-(5-methyl-1H-imidazol-4-yl)methyl-3-(3-cyanophenyl)-imidazolidin-2-one;
FCE 28278 means: 1-(5-methyl-1H-imidazol-4-yl)methyl-3-(3-methylthiophenyl)-imidazolidin-2-one;
FCE 28232 means: 1-(5-methyl-1H-imidazol-4-yl)methyl-3-(3,5-dichlorophenyl)-imidazolidin-2-one;
FCE 28355 means: 1-(5-methyl-1H-imidazol-4-yl)methyl-3-(3-methylphenyl)-imidazolidin-2-one;
FCE 28356 means: 1-(5-methyl-1H-imidazol-4-yl)methyl-3-(3,5-dimethylphenyl)-imidazolidin-2-one;
FCE 28307 means: 1-(1H-imidazol-4-yl)methyl-3-phenyl-imidazolidin-2-one.

In view of said activity, the compounds of the present invention can be useful, for example, in the treatment of CNS disorders such as, e.g., anxiety and psychosis, and/or in the treatment of gut motility disorders, and/or emesis. In view of the above activity, the compounds of the invention can be also useful as, for example, anti-migraine or antidrug addiction agents, or as cognition activators. The dosage level suitable for administration to adult humans of the compounds of the invention, either for prophylaxis or therapeutic treatment, may range from about 0.010 to about 20 mg/kg of body weight, depending on the chosen route of administration, on the particular compound chosen, on the particular patient under treatment and also on the nature and severity of the disorder. For instance for the compound of the invention 1-(5-methyl-1H-imidazol-4-yl)methyl-3-(3-chlorophenyl)-imidazolidin-2-one is suitable administered orally at a dosage in this range.

Preferably the compounds may be, e.g., administered in single or divided doses such that the total daily dosage falls within the range of about 0.020 to about 10 mg/kg per day.

Of course, these dosage regimens may be adjusted to provide the optimal therapeutic response.

The compounds of the invention can be administered in a variety of dosage forms, e.g. orally, in the form of tablets, capsules, sugar- or film-coated tablets, liquid solutions or suspensions.

The invention includes pharmaceutical compositions comprising a compound of the invention in association with a pharmaceutically acceptable excipient (which can be a carrier or diluent).

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions, or suspensions, tablets, pills, gelatine capsules, syrups, drops or suppositories.

Thus, for oral administration, the pharmaceutical composition containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/ or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following examples illustrate but do not limit the present invention.

EXAMPLE 1

1-(5-methyl-1-triphenylmethyl-1H-imidazol-4-yl)methyl-3-(3-chlorophenyl)-imidazolidin-2-one.

To a stirred solution of 1-(3-chlorophenyl)-imidazolidin-2-one (1.2 g; 0.0061 moles) in 20 ml of anhydrous dimethylformamide kept under nitrogen atmosphere, 50% NaH (0.3 g; 0.0062 moles) is added.

The solution is stirred for 1 hour at 60° C.; then 4-chloromethyl-5-methyl-1-triphenylmethyl-1H-imidazole (2.3 g; 0.0061 moles ) is added at room temperature. The mixture is stirred 6 hours at 90° C., then cooled, poured into water and extracted with methylene chloride. The organic layer is washed with brine, dried over anhydrous sodium sulfate and, after filtration, evaporated to dryness. The residue is purified by silica gel flash-chromatography (ethyl acetate as eluant) to give 2.1 g of the desired product as a white solid (m.p. 189°–191° C.; $C_{33}H_{29}ClN_4O$, required=C: 74.35; H: 5.48; N: 10.51; Cl: 6.65; found=C: 74.60; H: 5.55; N: 10.23; Cl: 6.43).

By proceeding analogously, the following compounds can be prepared:

1-(5-methyl-1-triphenylmethyl-1H-imidazol-4-yl)methyl-3-phenyl-imidazolidin-2-one, m.p. 196°–198° C.;

1-(5-methyl-1-triphenylmethyl-1H-imidazol-4-yl)methyl-3-(3-bromophenyl)-imidazolidin-2-one, m.p. 215°–217° C.;

1-(5-methyl-1-triphenylmethyl-1H-imidazol-4-yl)methyl-3-(4-chlorophenyl)-imidazolidin-2-one;

1-(5-methyl-1-triphenylmethyl-1H-imidazol-4-yl)methyl-3-(2-chlorophenyl)-imidazolidin-2-one;

1-(5-methyl-1-triphenylmethyl-1H-imidazol-4-yl)methyl-3-(3-cyanophenyl)-imidazolidin-2-one;

1-(5-methyl-1-triphenylmethyl-1H-imidazol-4-yl)methyl-3-(3-methylthiophenyl)-imidazolidin-2-one, m.p. 206° C. dec.;

1-(5-methyl-1-triphenylmethyl-1H-imidazol-4-yl)methyl-3(3-methylphenyl)-imidazolidin-2-one;

1-(5-methyl-1-triphenylmethyl-1H-imidazol-4-yl)methyl-3-(3,5-dimethylphenyl)-imidazolidin-2-one;

1-(5-methyl-1-triphenylmethyl-1H-imidazol-4-yl)methyl-3-(3,5-dichlorophenyl)-imidazolidin-2-one, m.p. 199°–202° C.;

1-(1-triphenylmethyl-1H-imidazol-4-yl)methyl-3-(3-chlorophenyl)-imidazolidin-2-one;

1-(1-triphenylmethyl-1H-imidazol-4-yl)methyl-3-phenyl-imidazolidin-2-one, m.p. 162°–166° C.;

1-(1-triphenylmethyl-1H-imidazol-4-yl)methyl-3-(3-bromophenyl)-imidazolidin-2-one;

1-(1-triphenylmethyl-1H-imidazol-4-yl)methyl-3-(3-cyanophenyl)-imidazolidin-Z-one; and 1-(1-triphenylmethyl-1H-imidazol-4-yl)methyl-3-(3-methylthiophenyl)-imidazolidin-2-one.

EXAMPLE 2

1-(5-methyl-1H-imidazol-4-yl)methyl-3-(3-chlorophenyl)imidazolidin-2-one.

A solution of 1-(5-methyl-1-triphenylmethyl-1H-imidazol-4-yl)methyl-3-(3-chlorophenyl)-imidazolidin-2-one (2 g; 0.0038 moles) in acetic acid (30 ml), water (30 ml) and tetrahydrofuran (30 ml) is heated at reflux for 1 hour. The solution is cooled and poured into 1N hydrochloric acid (100 ml) and washed with ethyl acetate.

The aqueous layer is basified with potassium carbonate (to pH 9) and extracted with methylene chloride. The organic layer is washed with brine and dried over anhydrous sodium sulfate and, after filtration, evaporated to dryness. The residue is triturated with dry diethyl ether to give 0.8 g of the desired product as a white solid (m.p. 229.5°–232.5° C. dec.; $C_{14}H_{15}ClN_4O$, required=C: 57.83; H: 5.20; N: 19.27; Cl: 12.20; found=C: 57.65; H: 5.32; N: 19.04; Cl: 12.53). By proceeding analogously, the following compounds can be prepared:

1-(5-methyl-1H-imidazol-4-yl)methyl-3-phenyl-imidazolidin-2-one, m.p. 207°–210.5° C.;

1-(5-methyl-1H-imidazol-4-yl)methyl-3-(3-bromophenyl)-imidazolidin-2-one, m.p. 233°–238.5° C.;

1-(5-methyl-1H-imidazol-4-yl)methyl-3-(3-cyanophenyl)-imidazolidin-2-one, m.p. 221°–226° C.;

1-(5-methyl-1H-imidazol-4-yl)methyl-3-(3-methylthiophenyl)-imidazolidin-2-one, m.p. 185°–190° C.;

1-(5-methyl-1H-imidazol-4-yl)methyl-3-(4-chlorophenyl)-imidazolidin-2-one, m.p. 230°–234° C.;

1-(5-methyl-1H-imidazol-4-yl)methyl-3-(2-chlorophenyl)-imidazolidin-2-one, m.p. 159.5°–167.5° C.;
1-(5-methyl-1H-imidazol-4-yl)methyl-3-(3-methylphenyl)-imidazolidin-2-one, m.p. 216°–221° C.;
1-(5-methyl-1H-imidazol-4-yl)methyl-3-(3,5-dimethylphenyl)-imidazolidin-2-one, m.p. 246°–249° C.;
1-(5-methyl-1H-imidazol-4-yl)methyl-3-(3,5-dichlorophenyl)-imidazolidin-2-one, m.p. 242°–249° C.;
1-(1H-imidazol-4-yl)methyl-3-(3-chlorophenyl)-imidazolidin-2-one;
1-(1H-imidazol-4-yl)methyl-3-phenyl-imidazolidin-2-one, m.p. 201°–203° C.;
1-(1H-imidazol-4-yl)methyl-3-(3-bromophenyl)-imidazolidin-2-one;
1-(1H-imidazol-4-yl)methyl-3-(3-cyanophenyl)-imidazolidin-2-one; and
1-(1H-imidazol-4-yl)methyl-3-(3-methylthiophenyl)-imidazolidin-2-one.

EXAMPLE 3

1-(5-methyl-1H-imidazol-4-yl)methyl-3-(3-chlorophenyl)-imidazolidin-2-one hydrochloride.

To a solution of 1-(5-methyl-1H-imidazol-4-yl)methyl-3-(3-chlorophenyl)-imidazolidin-2-one (0.6 g; 0.00206 moles) in absolute ethanol (10 ml) an excess of a solution of hydrochloric acid in ethanol is added.

Diethyl ether is added. The precipitate is filtered to give 0.65 g of the desired product as a white solid, 245° C. dec. By proceeding analogously, the following compounds can be prepared:
1-(5-methyl-1H-imidazol-4-yl)methyl-3-phenyl-imidazolidin-2-one hydrochloride;
1-(5-methyl-1H-imidazol-4-yl)methyl-3-(3-bromophenyl)-imidazolidin-2-one hydrochloride;
1-(5-methyl-1H-imidazol-4-yl)methyl-3-(3-cyanophenyl)-imidazolidin-2-one hydrochloride;
1-(5-methyl-1H-imidazol-4-yl)methyl-3-(3-methylthiophenyl)-imidazolidin-2-one hydrochloride;
1-(5-methyl-1H-imidazol-4-yl)methyl-3-(3-methylphenyl)-imidazolidin-2-one hydrochloride;
1-(5-methyl-1H-imidazol-4-yl)methyl-3-(3,5-dimethylphenyl)-imidazolidin-2-one hydrochloride;
1-(5-methyl-1H-imidazol-4-yl)methyl-3-(3,5-dichlorophenyl)-imidazolidin-2-one hydrochloride;
1-(5-methyl-1H-imidazol-4-yl)methyl-3-(4-chlorophenyl)-imidazolidin-2-one hydrochloride;
1-(5-methyl-1H-imidazol-4-yl)methyl-3-(2-chlorophenyl)-imidazolidin-2-one hydrochloride;
1-(1H-imidazol-4-yl)methyl-3-(3-chlorophenyl)-imidazolidin-2-one hydrochloride;
1-(1H-imidazol-4-yl)methyl-3-phenyl-imidazolidin-2-one hydrochloride;
1-(1H-imidazol-4-yl)methyl-3-(3-bromophenyl)-imidazolidin-2-one hydrochloride;
1-(1H-imidazol-4-yl)methyl-3-(3-cyanophenyl)-imidazolidin-2-one hydrochloride; and
1-(1H-imidazol-4-yl)methyl-3-(3-methylthiophenyl)-imidazolidin-2-one hydrochloride.

EXAMPLE 4

1-(1-ethyl-4-methyl-1H-imidazol-5-yl)methyl-3-phenyl-imidazolidin-2-one hydrochloride.

To a solution of 1-(5-methyl-1H-imidazol-4-yl)methyl-3-phenyl-imidazolidin-2-one (1 g; 0.0039 moles in 20 ml of anhydrous dimethylformamide kept under nitrogen atmosphere, 50% NaH (0.198 g; 0.0041 moles) is added at 0° C. After 15 min, ethyl iodide (0.33 ml; 0.0041 moles) is added and stirring is continued for 1 h at room temperature. The mixture cooled at 0° C. is poured into water and extracted with methylene chloride.

The organic layer is washed with brine, dried over anhydrous sodium sulfate and, after filtration, evaporated to dryness. The residue is purified by silica gel flash-chromatography (ethyl acetate-methanol-30% ammonium hydroxide, 190:10:3 as eluant) and treated with an excess of a solution of hydrochloric acid in ethanol. The crude salt is collected by filtration and recrystallized from absolute ethanol to yield 0.21 g of the desired product as a white solid; m.p. 227°–230° C.

By proceeding analogously, the following compounds can be prepared:
1-(1-ethyl-4-methyl-1H-imidazol-5-yl)methyl-3-(3-chlorophenyl)-imidazolidin-2-one hydrochloride;
1-(1,4-dimethyl-1H-imidazol-5-yl)methyl-3-(3-chlorophenyl)-imidazolidin-2-one hydrochloride; and
1-(1,4-dimethyl-1H-imidazol-5-yl)methyl-3-phenyl-imidazolidin-2-one hydrochloride.

EXAMPLE 5

1-(1-ethyl-5-methyl-1H-imidazol-4-yl)methyl-3-phenyl-imidazolidin-2-one hydrochloride.

The flash-chromatography of Example 4 gives a second eluted, which is treated with an excess of a solution of hydrochloric acid in ethanol. The crude salt is collected by filtration and recrystallized from absolute ethanol to yield 0.4 g of the captioned product as a white solid, m.p. 225°–230° C. By proceeding analogously, the following compounds can be prepared:
1-(1-ethyl-5-methyl-1H-imidazol-4-yl)methyl-3-(3-chlorophenyl)-imidazolidin-2-one hydrochloride;
1-(1,5-dimethyl-1H-imidazol-4-yl)methyl-3-(3-chlorophenyl)-imidazolidin-2-one hydrochloride; and
1-(1,5-dimethyl-1H-imidazol -4-yl) methyl-3-phenyl-imidazolidin-2-one hydrochloride.

EXAMPLE 6

Tablets each weighing 150 mg and containing 60 mg of the active substance can be manufactured by blending and compressing the following ingredients:

| | |
|---|---|
| 1-(5-methyl-1H-imidazol-4-yl)methyl-3-(3-chlorophenyl)-imidazolidin-2-one | 60 mg |
| Starch | 50 mg |
| Cellulose microcrystalline | 30 mg |
| Polyvinylpyrrolidone | 5 mg |
| Sodium carboxymethyl starch | 4.5 mg |
| Magnesium stearate | 0.5 mg |

EXAMPLE 7

Capsules, each dosed at 200 mg and containing 80 mg of the active substance can be prepared as follows:

| | |
|---|---|
| 1-(5-methyl-1H-imidazol-4-yl)methyl-3-(3-chlorophenyl)-imidazolidin-2-one | 80 mg |
| Corn starch | 60 mg |
| Cellulose microcrystalline | 59 mg |
| Magnesium stearate | 1 mg |

We claim:

1. A compound having formula (I)

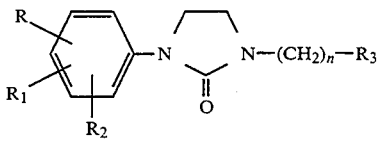

wherein n is 1, 2 or 3;

each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxycarbonyl, nitro, —$N(R_4R_5)$ in which each of $R_4$ and $R_5$ independently is hydrogen, $C_1$–$C_6$ alkyl, formyl or $C_2$–$C_6$ alkanoyl; or a $(R_6R_7)N$—$SO_2$ group, in which each of $R_6$ and $R_7$ independently is hydrogen or $C_1$–$C_6$ alkyl;

$R_3$ is an imidazolyl group of formula

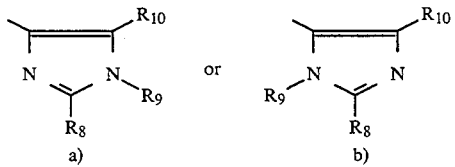

wherein each of $R_8$ and $R_{10}$ which may be the same or different is hydrogen or $C_1$–$C_6$ alkyl, $R_9$ is hydrogen, $C_1$–$C_6$ alkyl, triphenylmethyl, t-butyloxycarbonyl, benzyloxycarbonyl, acetyl, formyl, di(p-methoxyphenyl)-methyl or (p-methoxyphenyl) diphenylmethyl; or a pharmaceutically acceptable salt thereof.

2. A compound of formula (I), according to claim 1, wherein each of R, $R_1$ and $R_2$, which may be the same or different, is hydrogen, halogen, cyano, $CF_3$, $C_1$–$C_4$ alkylthio, $C_1$–$C_4$ alkoxy or —$N(R_4 R_5)$ in which each of $R_4$ and $R_5$ independently is hydrogen, $C_1$–$C_4$ alkyl, formyl or $C_2$–$C_4$ alkanoyl;

n is 1 or 2;

$R_3$ is as defined above;

each of $R_8$, $R_9$ and $R_{10}$ is independently hydrogen or $C_1$–$C_4$ alkyl; or a pharmaceutically acceptable salt thereof.

3. A compound selected from the group consisting of
1-(5-methyl-1H-imidazol-4-yl)methyl-3-(3-chlorophenyl)-imidazolidin-2-one;
1-(5-methyl-1H-imidazol-4-yl)methyl-3-phenyl-imidazolin-2-one;
1-(5-methyl-1H-imidazol-4-yl)methyl-3-(3-bromophenyl)-imidazolidin-2-one;
1-(5-methyl-1H-imidazol-4-yl)methyl-3-(3-cyanophenyl)-imidazolidin-2-one;
1-(5-methyl-1H-imidazol-4-yl)methyl-3-(3-methylthiophenyl)-imidazolidin-2-one;
1-(5-methyl-1H-imidazol-4-yl)methyl-3-(3-methylphenyl)-imidazolidin-2-one;
1-(5-methyl-1H-imidazol-4-yl)methyl-3-(3,5-dimethylphenyl)-imidazolidin-2-one;
1-(5-methyl-1H-imidazol-4-yl)methyl-3-(3,5-dichlorophenyl)-imidazolidin-2-one;
1-(1H-imidazol-4-yl)methyl-3-(3-chlorophenyl)-imidazolidin-2-one;
1-(1H-imidazol-4-yl)methyl-3-phenyl-imidazolidin-2-one;
1-(1H-imidazol-4-yl)methyl-3-(3-bromophenyl)-imidazolidin-2-one;
1-(1H-imidazol-4-yl)methyl-3-(3-cyanophenyl)-imidazolidin-2-one;
1-(1H-imidazol-4-yl)methyl-3-(3-methylthiophenyl)-imidazolidin-2-one;
or a pharmaceutically acceptable salt thereof.

4. The salt of a compound according to claim 1, wherein said salt is the hydrochloride.

5. A pharmaceutical composition comprising a suitable carrier and/or diluent and, as an active principle, an effective amount of a compound of formula (I) or a pharmaceutically acceptable salt thereof as defined in claim 1.

6. A method of producing a $5HT_3$ receptor antagonistic effect in a patient in need of such effect, said method comprising administering to the patient a $5HT_3$ receptor antagonistic-effective amount of a compound of claim 1.

* * * * *

UNITED STATES PATENT AND TRADEMARK OFFICE
CERTIFICATE OF CORRECTION

PATENT NO. : 5,424,328
DATED : June 13, 1995
INVENTOR(S) : VARASI et al

It is certified that error appears in the above-indentified patent and that said Letters Patent is hereby corrected as shown below:

Column 5, Table 1, second line after "anesthetized" insert --Rat--.

Column 5, line 59, after "Table II." insert the following:

-- TABLE II

"5.HT$_3$, Receptor Binding Test"
--.

Column 8, line 33, change "-imidazolidin-Z-one" to --imidazolidin-2-one;--.

Signed and Sealed this

Fifth Day of March, 1996

BRUCE LEHMAN

Attest:

Attesting Officer

Commissioner of Patents and Trademarks